US011344181B2

(12) United States Patent
 Nakazato (10) Patent No.: US 11,344,181 B2
(45) Date of Patent: May 31, 2022

(54) ENDOSCOPE TIP ATTACHMENT

(71) Applicant: OLYMPUS CORPORATION, Tokyo (JP)

(72) Inventor: Takeharu Nakazato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 522 days.

(21) Appl. No.: 16/249,202

(22) Filed: Jan. 16, 2019

(65) Prior Publication Data

US 2019/0150710 A1 May 23, 2019

Related U.S. Application Data

(63) Continuation of application No. PCT/JP2017/011279, filed on Mar. 21, 2017.

(30) Foreign Application Priority Data

Jul. 19, 2016 (JP) .............................. JP2016-141787

(51) Int. Cl.
*A61B 1/00* (2006.01)
*A61B 8/12* (2006.01)
(Continued)

(52) U.S. Cl.
CPC ...... *A61B 1/00089* (2013.01); *A61B 1/00068* (2013.01); *A61B 1/00087* (2013.01);
(Continued)

(58) Field of Classification Search
CPC .............. A61B 1/0008; A61B 1/00089; A61B 1/00091; A61B 1/00098; A61B 1/00101;
(Continued)

(56) References Cited

U.S. PATENT DOCUMENTS 5,090,433 A * 2/1992 Kamaga ................. A61B 1/122
134/182
5,460,168 A * 10/1995 Masubuchi ........ A61B 1/00098
600/107
(Continued)

FOREIGN PATENT DOCUMENTS

CN 102813496 A 12/2012
JP 58-133230 A 8/1983
(Continued)

OTHER PUBLICATIONS

Chinese Office Action dated Nov. 13, 2020 received in 201780044503.0.

(Continued)

*Primary Examiner* — Ryan N Henderson
(74) *Attorney, Agent, or Firm* — Scully, Scott, Murphy & Presser, P.C.

(57) ABSTRACT

An endoscope tip attachment includes: a cylindrical casing that is arranged to surround a distal end portion of an endoscope that includes a raising base to raise a treatment tool; and a fluid controller that is positioned at an opening of a treatment-tool insertion channel of the endoscope inside the casing in a state in which the casing is attached to the distal end portion of the endoscope, the fluid controller being configured to control a flow of solution that has flowed from the treatment-tool insertion channel of the endoscope toward the distal end portion of the endoscope to flow equally along an entire surface of the raising base provided at the distal end portion of the endoscope, and being movable by pressure received from the solution.

10 Claims, 9 Drawing Sheets

(51) Int. Cl.
*A61B 8/00* (2006.01)
*A61B 1/12* (2006.01)

(52) U.S. Cl.
CPC ...... *A61B 1/00098* (2013.01); *A61B 1/00101* (2013.01); *A61B 1/00135* (2013.01); *A61B 1/122* (2013.01); *A61B 1/125* (2013.01); *A61B 1/126* (2013.01); *A61B 8/12* (2013.01); *A61B 8/445* (2013.01)

(58) Field of Classification Search
CPC ............ A61B 1/00131; A61B 1/00133; A61B 1/0014; A61B 1/00119; A61B 1/00128; A61B 1/00135; A61B 1/00142; A61B 1/015; A61B 1/12; A61B 1/121–123; A61B 1/125–127; A61B 1/00068; A61B 8/12; A61B 8/445
See application file for complete search history.

(56) References Cited

U.S. PATENT DOCUMENTS

| | | | | |
|---|---|---|---|---|
| 9,993,145 B2* | 6/2018 | Yamaya | ............. | A61B 1/00098 |
| 10,004,390 B2 | 6/2018 | Yamaya | | |
| 10,188,268 B2* | 1/2019 | Hiraoka | ............. | A61B 1/00098 |
| 10,548,462 B2* | 2/2020 | Jiang | ............. | A61B 46/13 |
| 10,856,724 B2* | 12/2020 | Miller | ............. | A61B 1/126 |
| 11,019,984 B2* | 6/2021 | Miller | ............. | A61B 1/00101 |
| 2002/0065450 A1* | 5/2002 | Ogawa | ............. | A61B 1/126 600/157 |
| 2007/0112249 A1* | 5/2007 | Yamaya | ............. | A61B 1/00098 600/107 |
| 2009/0215160 A1* | 8/2009 | Hatori | ............. | A61L 2/28 435/287.4 |
| 2012/0316394 A1 | 12/2012 | Yoshida et al. | | |
| 2014/0358089 A1* | 12/2014 | Kappel | ............. | A61B 1/00089 604/176 |
| 2016/0338681 A1* | 11/2016 | Smith | ............. | A61B 1/00089 |
| 2017/0127916 A1* | 5/2017 | Hiraoka | ............. | A61B 1/00098 |
| 2017/0150877 A1* | 6/2017 | Yamaya | ............. | A61B 1/00128 |
| 2017/0181611 A1* | 6/2017 | Yamaya | ............. | A61B 1/125 |
| 2017/0181612 A1* | 6/2017 | Yamaya | ............. | A61B 1/00009 |
| 2018/0206708 A1* | 7/2018 | Miller | ............. | A61B 1/015 |

FOREIGN PATENT DOCUMENTS

| | | |
|---|---|---|
| JP | 7-31001 U | 6/1995 |
| JP | 7-255666 A | 10/1995 |
| JP | 2015-181914 A | 10/2015 |
| WO | 2016/059920 A1 | 4/2016 |
| WO | 2016/059921 A1 | 4/2016 |

OTHER PUBLICATIONS

International Search Report dated Jun. 13, 2017 received in PCT/JP2017/011279.

* cited by examiner

ENDOSCOPE TIP ATTACHMENT

CROSS-REFERENCE TO RELATED APPLICATION

This application is a continuation of PCT International Application No. PCT/JP2017/011279 filed on Mar. 21, 2017 which claims the benefit of priority from Japanese Patent Application No. 2016-141787, filed on Jul. 19, 2016, the entire contents of which are incorporated herein by reference.

BACKGROUND

1. Technical Field

The present disclosure relates to an endoscope tip attachment that is attached to a distal end of an endoscope.

2. Related Art

Endoscopes require to be cleaned and sterilized at each use. For example, Japanese Laid-open Patent Publication No. 7-255666 describes that a portion at which a forceps raising base is arranged at a distal end of an endoscope is cleaned by using a syringe jetting out cleaning solution when an endoscope is cleaned.

SUMMARY

In some embodiments, an endoscope tip attachment includes: a cylindrical casing that is arranged to surround a distal end portion of an endoscope that includes a raising base to raise a treatment tool; and a fluid controller that is positioned at an opening of a treatment-tool insertion channel of the endoscope inside the casing in a state in which the casing is attached to the distal end portion of the endoscope, the fluid controller being configured to control a flow of solution that has flowed from the treatment-tool insertion channel of the endoscope toward the distal end portion of the endoscope to flow equally along an entire surface of the raising base provided at the distal end portion of the endoscope, and being movable by pressure received from the solution.

The above and other features, advantages and technical and industrial significance of this disclosure will be better understood by reading the following detailed description of presently preferred embodiments of the disclosure, when considered in connection with the accompanying drawings.

DETAILED DESCRIPTION

An endoscope tip attachment in a form (hereinafter, "embodiment") to implement the disclosure is specifically explained hereafter, referring to the drawings.

1. First Embodiment

An endoscope tip attachment according to a first embodiment is explained, referring to FIG. 1 to FIG. 7. A structure of an endoscope to which the endoscope tip attachment is attached is first explained herein, and a structure of the endoscope tip attachment is subsequently explained.

1-1. Endoscope

Figure 1:
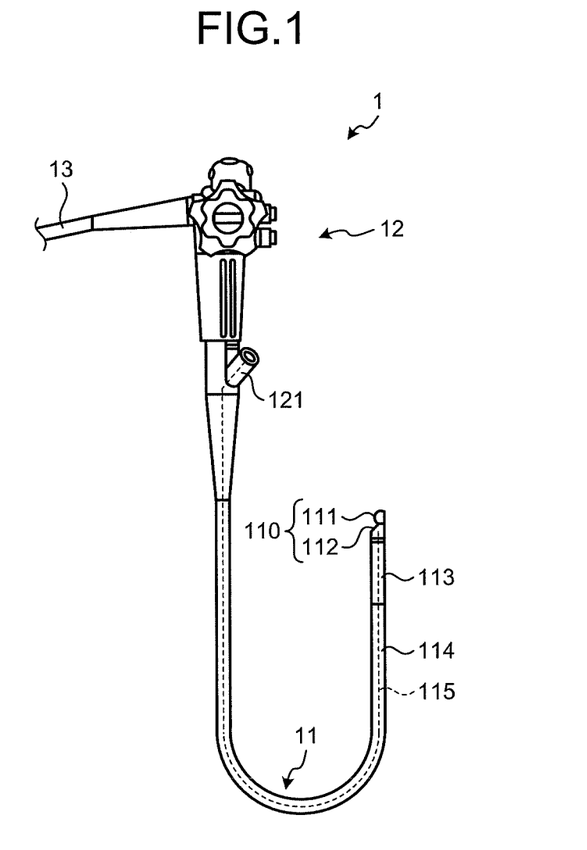
FIG. 1 schematically shows an example of an endoscope.
Figure 2:
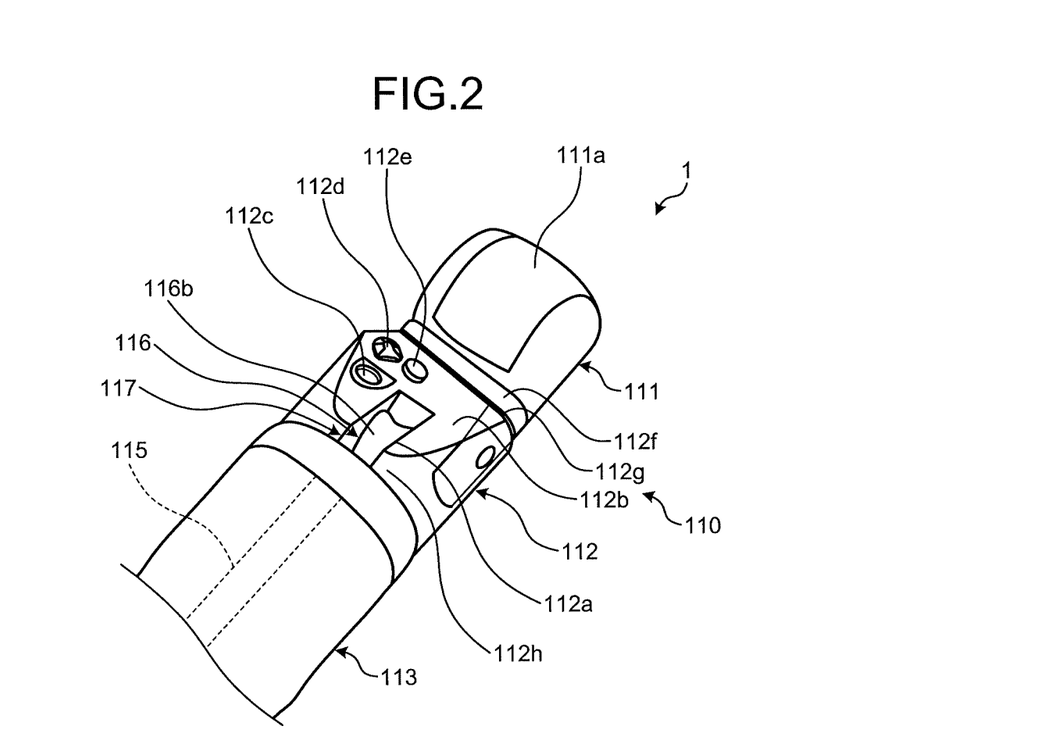
FIG. 2 is a perspective view schematically showing a structure of a distal end portion of the endoscope.

FIG. 1 schematically shows an example of the endoscope. FIG. 2 is a perspective view schematically showing a structure of a distal end portion of the endoscope. An endoscope 1 shown in FIG. 1 and FIG. 2 is an ultrasound endoscope that transmits ultrasonic waves to a subject to be observed, and that receives ultrasonic waves reflected by the subject.

As shown in FIG. 1, the endoscope 1 includes a tubular insertion portion 11 to be inserted into a subject, an operation portion 12 that is provided at a proximal end portion of the insertion portion 11, and that is held by a user and accepts an operation input from the user, and a universal cord 13 that extends from the operation portion. The universal cord 13 includes plural signal cables, an optical fiber that transmits illumination light generated by a light source device (not shown), and the like.

The insertion portion 11 includes a distal end portion (distal end hard portion) 110, an exterior of which is covered with a hard member, a bending portion 113 that can be bent according to an operation input accepted by the operation portion 12, and a flexible tube portion 114, an exterior of which is covered with a member having flexibility. The distal end portion 110 is constituted of a first hard portion 111 that includes an ultrasound probe 111a (shown in FIG. 2), and a second hard portion 112 that includes an optical component. Moreover, inside the insertion portion 11, a treatment tool channel 115 that is a channel to insert therein a treatment tool, such as a forceps and a puncture needle, is formed. A structure of the distal end portion 110 is described later with reference to FIG. 2.

In the operation portion 12, a treatment tool inlet 121 to insert a treatment tool is provided. A treatment tool is inserted through the treatment tool inlet 121 to the treatment tool channel 115, and protrudes outside from a treatment tool opening 112a (shown in FIG. 2) that is formed in the second hard portion 112 of the distal end portion 110.

Although not shown, a connector is arranged at an end portion of the universal cord 13 on the opposite side to the operation portion 12. The universal cord 13 is connected to an ultrasound observation apparatus, a camera control unit, a display device, a light source device, and the like (not shown) via the connector. Furthermore, inside the insertion portion 11, a light guide that transmits illumination light supplied by the light source device and multiple signal cables that transmit various kinds of signals are arranged.

As shown in FIG. 2, in the distal end portion 110, the first hard portion 111 on a distal end side and the second hard portion 112 on a proximal end side are joined. In the first hard portion 111, the convex ultrasound probe 111a is provided on the distal end side. The first hard portion 111 protrudes toward the distal end side from the second hard portion 112. The ultrasound probe 111a is not limited to be of a convex type, but can be of a linear type also.

The second hard portion 112 has an inclined portion 112b that inclines toward the proximal end side from the distal end side. In the inclined portion 112b, the treatment tool opening 112a that communicates with the treatment tool channel 115, an objective lens 112c that collects light from outside to guide it to an imaging optical system, an illumination lens 112d that is positioned on distal end side of the light guide and emits illumination light, and air/water supply nozzle 112e are provided.

The treatment tool opening 112 is an opening on the distal end side of the treatment tool channel 115, and opens to part of the inclined portion 112b. Inside the treatment tool opening 112a, a raising base 116 enabled to change a protrusion direction of a treatment tool is arranged. By an operation input to the operation portion 12, the raising base 116 rotates to change a raising angle. The raising base 116 rotates about a supporting axis 116a shown in FIG. 7 described later to switch between a raised state and a laid state of a portion on the distal end side.

As shown in FIG. 2, the raising base 116 includes a mounting surface 116b on which at treatment tool is put on, and is housed inside a housing room 117 formed in the second hard portion 112. The housing room 117 is space, a distal-end-side opening of which is the treatment tool opening 112a, and a proximal-end-side opening (not shown) of the housing room 117 communicates with the treatment tool channel 115. The raising base 116 inside the housing room 117 is arranged such that the mounting surface 116b faces toward the treatment tool opening 112a.

Moreover, at a distal end portion of the second hard portion 112, a neck portion 112f that is a part joining with the first hard portion 111 is arranged. The neck portion 112f is a tubular member, and holds the signal cable connected to the ultrasound probe 111a, an insulating pipe wrapping the signal cable, and the like therein. On an outer peripheral portion of the neck portion 112f, a balloon groove 112g is arranged around an entire perimeter thereof. The balloon groove 112g is a ring-shaped groove, and is a portion in which a band portion of a balloon fits when a balloon is attached to the endoscope 1. Ata cleaning of the endoscope 1, an endoscope tip attachment 2 (shown in FIG. 3) fits in the balloon groove 112g.

On the other hand, at a proximal end portion of the second hard portion 112, a non-inclined portion 112h that is a part joining with the bending portion 113 is arranged. The non-inclined portion 112h has an outer peripheral portion in a cylindrical shape extending from a proximal end side toward a distal end side, and is formed on the proximal end side relative to the inclined portion 112b. In the non-inclined portion 112h, part of the treatment tool opening 112a is arranged.

1-2. Attachment

Figure 3:
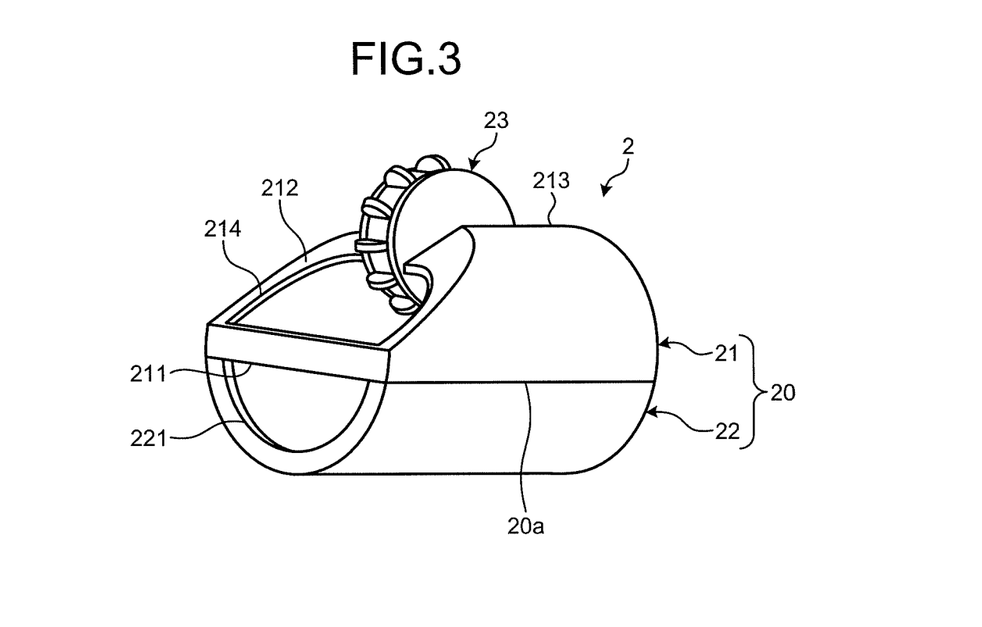
FIG. 3 is a perspective view schematically showing an entire structure of an endoscope tip attachment according to a first embodiment.
Figure 4:
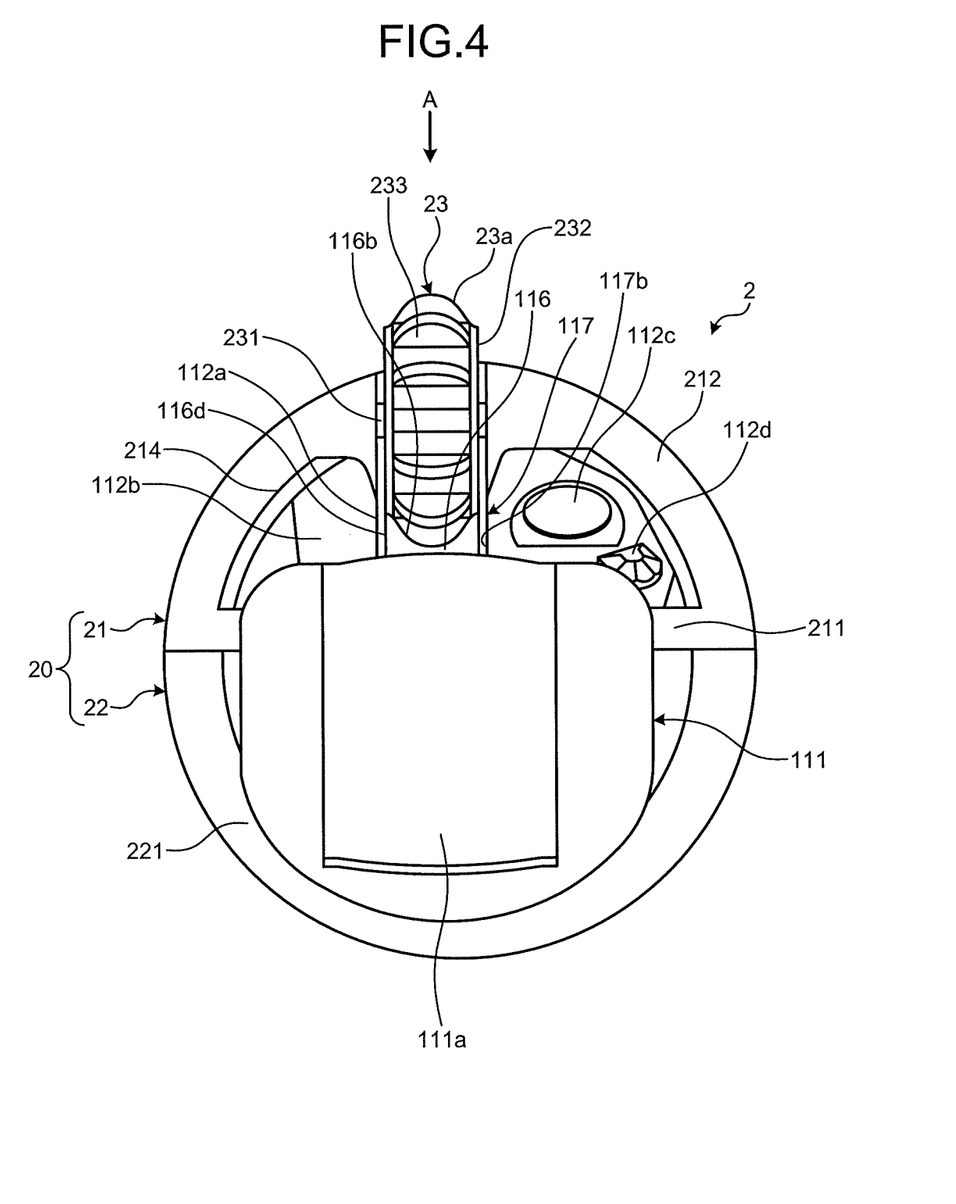
FIG. 4 schematically shows a state in which the endoscope tip attachment according to the first embodiment is attached to the distal end portion of the endoscope, viewed from a distal end side.
Figure 5:
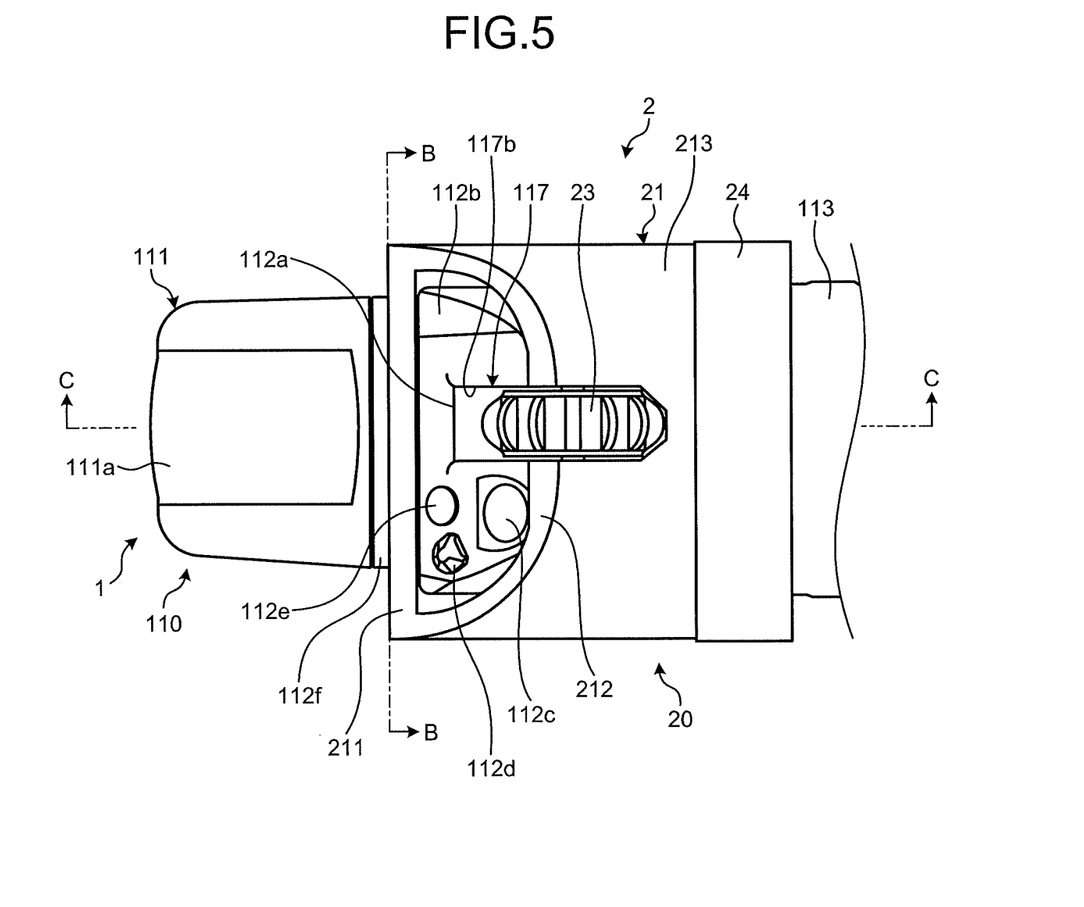
FIG. 5 shows a view from a direction of an arrow A in FIG. 4.
Figure 6:
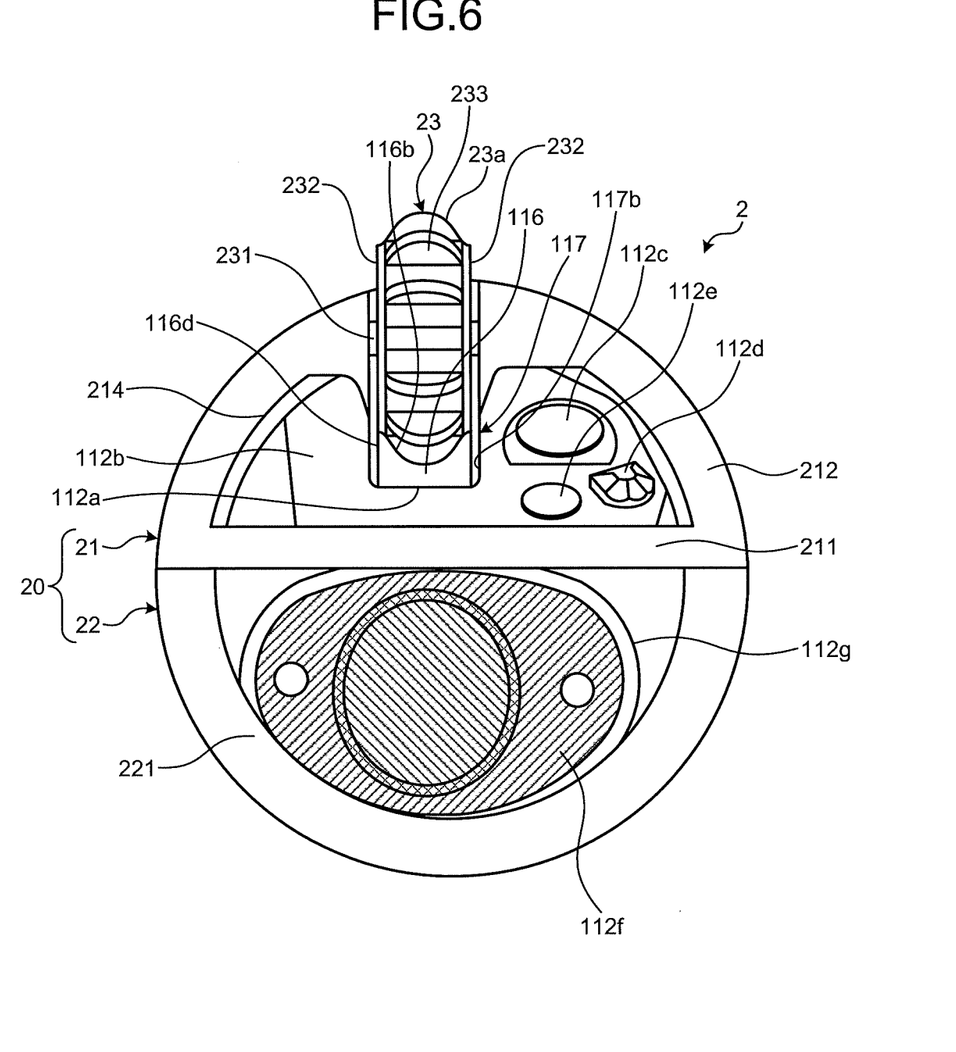
FIG. 6 is a partial cross-section including a section taken along a line B-B in FIG. 5.
Figure 7:
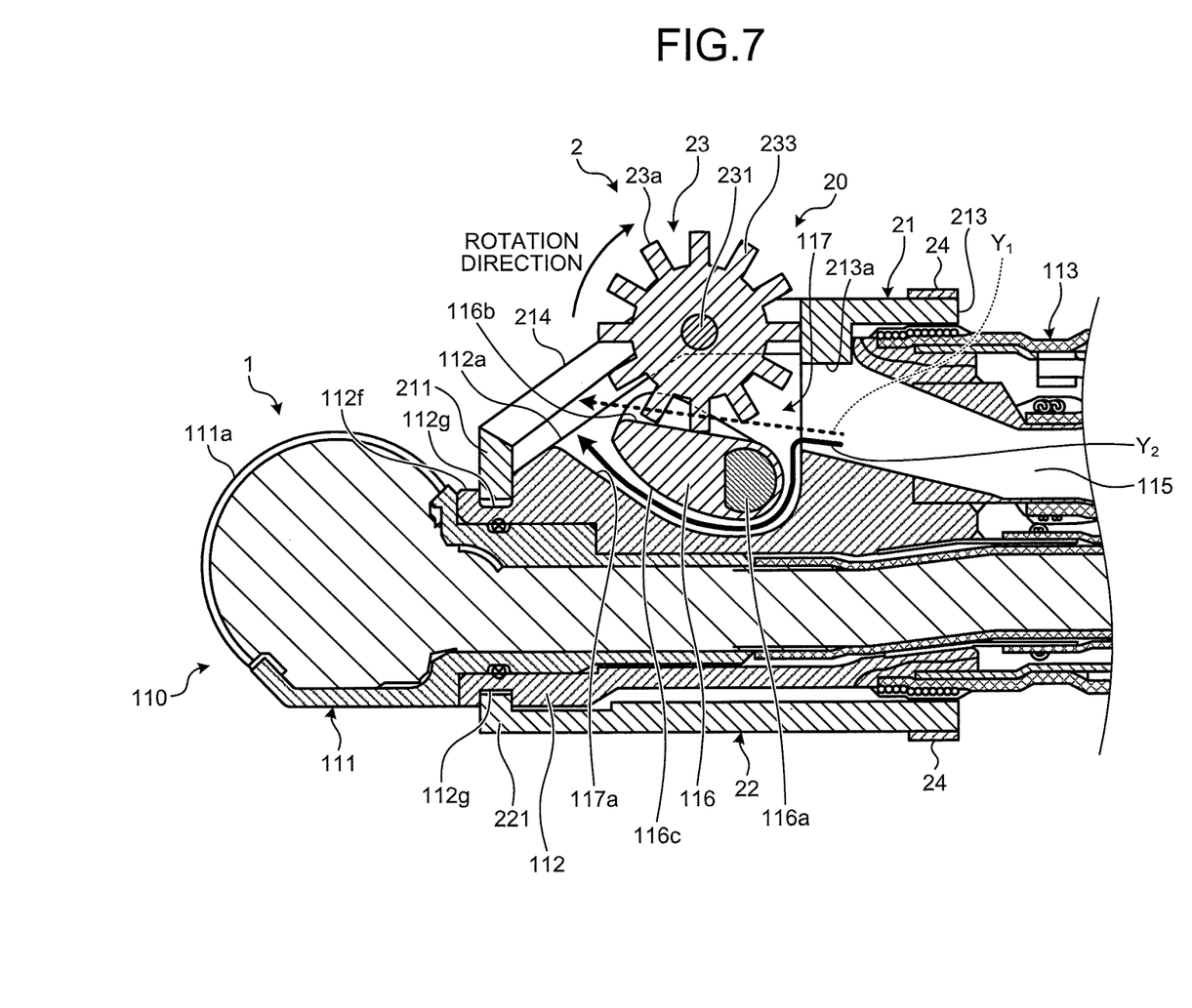
FIG. 7 is a cross-section taken along a line C-C in FIG. 5.

Next, a structure of the endoscope tip attachment 2 is explained, referring to FIG. 3 to FIG. 7. FIG. 3 is a perspective view schematically showing an entire structure of the endoscope tip attachment 2 according to the first embodiment. FIG. 4 schematically shows a state in which the endoscope tip attachment 2 according to the first embodiment is attached to the distal end portion 110 of the endoscope 1, viewed from the distal end side. FIG. 5 shows a view from a direction of an arrow A in FIG. 4. FIG. 6 is a partial cross-section including a section taken along a line B-B in FIG. 5. FIG. 7 is a cross-section taken along a line C-C in FIG. 5.

As shown in FIG. 3, the endoscope tip attachment (hereinafter, simply "attachment") 2 in the first embodiment includes a tubular casing 20 that has openings at both ends, and a water wheel 23 as a fluid controller. The fluid controller is a member that controls a flow of solution inside the casing at cleaning of the endoscope 1, and is a movable member that is moved by pressure applied by solution.

The casing 20 includes a first casing 21 to which the water wheel 23 is attached, and a second casing 22 that is detachable with respect to the first casing 21 at a joint portion 20a. The casing 20 is structured to be separated into two pieces at the joint portion 20a. In a state in which the attachment 2 is attached to the distal end portion 110 of the endoscope 1, the first casing 21 and the second casing 22 are connected into one piece with the joint portion 20a. When the attachment 2 is removed from the distal end portion 110 of the endoscope 1, the first casing 21 and the second casing 22 are separated at the joint portion 20a. For example, the joint portion 20a includes an engaging portion (not shown) in concave and convex shapes respectively arranged at end portions in a perimeter direction of the respective casings 21, 22. In this explanation, a state in which the attachment 2 is attached to the distal end portion 110 of the endoscope 1 is described as "attached state", and "cleaning solution" is simply described as "solution".

The first casing 21 includes a first fitting portion 211 in which the distal end portion 110 of the endoscope 1 fits, an inclined portion 212 that is inclined from the distal end side toward the proximal end side, and a semicylindrical portion 213 that forms a portion on the proximal end side relative to the inclined portion 212. The first fitting portion 211 is formed by a portion in the distal end portion of the first casing 21 linearly extending in a diameter direction of the casing 20. The first fitting portion 211 is a positioning portion that comes in contact with the distal end portion 110 of the endoscope 1, and fits in the balloon groove 112g of the endoscope 1. The inclined portion 212 has a shape that is inclined along the inclined portion 112b of the endoscope 1. In the inclined portion 212, an opening window 214 that is formed with a through hole is arranged. In the attached state, the inclined portion 212 of the first casing 21 faces the inclined portion 112b of the endoscope 1, and solution to clean the endoscope 1 flows outside of the casing 20 through the opening window 214. The semicylindrical portion 213 is arranged on an outer periphery side of the non-inclined portion 112h of the second hard portion 112 in the attached state.

The second casing 22 is formed in a semicylindrical shape as its entire shape, and includes a second fitting portion 221 that fits with the distal end portion 110 of the endoscope 1. The second fitting portion 221 is formed by a portion in the distal end portion of the second casing 22 protruding toward the inside in a diameter direction of the casing 20. The second fitting portion 221 is a positioning portion that comes in contact with the distal end portion 110 of the endoscope 1, and fits in the balloon groove 112g of the endoscope 1. The second casing 22 is arranged to cover a rear surface of the second hard portion 112 in the attached state.

The water wheel 23 is rotatably arranged to make relative rotation with respect to the first casing 21 in a state in which part thereof is positioned outside the casing 20. At cleaning of the endoscope 1, the water wheel 23a receives pressure from solution to obtain a rotation torque to rotate.

As shown in FIG. 4, the water wheel 23 includes a supporting axis 231 that is attached to the first casing 21, two pieces of rotating plates 232 in a disk shape that are supported by the supporting axis 231, and a blade wheel 233 that is sandwiched between the two pieces of rotating plates 232 and has plural blades arranged at uniform intervals along a perimeter direction of the rotating plates 232. The supporting axis 231, the two pieces of rotating plates 232, and the blade wheel 233 rotate together.

The supporting axis 231 penetrates through the two pieces of rotating plates 232 at the center, and is arranged such that both end portions are rotatable to make relative rotation with respect to the first casing 21, on outer sides of the respective rotating plates 232. The two pieces of rotating plates 232 are arranged to sandwich the blade wheel 233 from respective sides in an axial direction of the supporting axis 231. The blade wheel 233 is a portion that receives solution at cleaning, and is supported by the supporting axis 231. The blades included in the blade wheel 233 are all protruded outward in a diameter direction from an outer diameter of the rotating plates 232. An outer periphery portion 23a of the water wheel 23 is formed in a curved shape in which a diameter gradually increases from respective end sides toward a center side in the axial direction of the supporting axis 231.

The outer periphery portion 23a of the water wheel 23 is structured to be able to come in contact with the mounting surface 116b of the raising base 116 inside the casing 20 in the attached state. As shown in FIG. 4, the mounting surface 116b of the raising base 116 is formed to have a curved surface in which a central portion is recessed compared to both end portions in a width direction of the raising base 116 (the axial direction of the supporting axis 231) when the endoscope 1 is viewed from the distal end side. The outer periphery portion 23a of the water wheel 23 has a shape that a central portion rises compared to both end portions in a width direction thereof. That is, the outer periphery portion 23a of the water wheel 23 is formed in a shape along (shape corresponding to) the mounting surface 116b to be in contact in the axial direction of the supporting axis 231. When the outer periphery portion 23a of the water wheel 23 and the raising base 116 are able to be in contact with each other, the blades of the blade wheel 233 are structured with flexible members. In this case, when the water wheel 23 rotates, the outer periphery portion 23a of the water wheel 23 having flexibility can slide on the mounting surface 116b of the raising base 116.

As shown in FIG. 5, in the attached state, the attachment 2 is arranged to surround the distal end portion 110 (at least the second hard portion 112) of the endoscope 1. The ultrasound probe 111a is positioned outside the casing 20, and the raising base 116 is positioned inside the casing 20. A distal end portion of the attachment 2 is structured in a form in which the treatment tool opening 112a is seen through the opening window 214 of the first casing 21. The opening window 214 is arranged between a portion at which the water wheel 23 is attached and the first fitting portion 211. The opening window 214 is formed in a shape in which a part thereof is curved to be narrower toward the proximal end side from the distal end side. Furthermore, the semicylindrical portion 213 that is a proximal end portion of the attachment 2 is fastened on an outer periphery portion of the non-inclined portion 112h of the second hard portion 112 by an elastic ring-shaped member 24. The ring-shaped member 24 is constituted of a rubber band or the like.

As shown in FIG. 6, the first fitting portion 211 in a straight shape fits in a part of the balloon groove 112g, which is an annular groove. On the other hand, the second fitting portion 221 in a curved shape fits in a part of the balloon groove 112g different from the part in which the first fitting portion 211 fits. Thus, the attachment 2 is engaged therein not to move toward a distal end direction and a proximal end direction with respect to the endoscope 1 in the attached state.

Referring to FIG. 7, a flow of solution at cleaning is explained herein. First, a case in which the attachment 2 is not attached to the distal end portion 110 of the endoscope 1 is explained for comparison. In this case, solution flowing out from the opening of the treatment tool channel 115 flows along the mounting surface 116b of the raising base 116 inside the housing room 117 as indicated by an arrow $Y_1$ in a broken line in FIG. 7. Because the solution inside the casing 20 flows smoothly in a direction of the arrow $Y_1$, the solution flows outside the casing 20 through the opening window 214 from the distal end side of the mounting surface 116b. That is, without the attachment 2, as indicated by an arrow $Y_2$ in a solid line in FIG. 7, it is unlikely that a situation in which the solution flows in a gap between a rear surface 116c of the raising base 116 and a bottom surface 117a of the housing room 117 occurs. The rear surface 116c is a surface opposite to the mounting surface 116b.

On the other hand, in the attached state of the attachment 2, the water wheel 23 that is a fluid controller is positioned at the opening of the treatment tool channel 115. In more detail, only one side of the blade of the blade wheel 233 faces the opening of the treatment tool channel 115. A position at which the blades of the blade wheel 233 is positioned is a position to restrain a direction (indicated by the arrow $Y_1$) in which solution flowing out from the opening of the treatment tool channel 115 flows toward the distal end side along the mounting surface 116b of the raising base 116. That is, one side of the blade of the blade wheel 233 is a pressure receiving surface that receives pressure of solution flowing out from the opening of the treatment tool channel 115 in the direction of the arrow $Y_1$. Furthermore, the water wheel 23 is structured to have a rotational resistance to a flow of solution. For example, the supporting axis 231 is attached to slide on the first casing 21 to generate a rotational resistance of the water wheel 23. Therefore, it is possible to restrain smooth flow of solution that has flowed out from the opening of the treatment tool channel 115 along the mounting surface 116b of the raising base 116 inside the housing room 117 by the water wheel 23. Thus, the solution inside the housing room 117 is likely to flow in the gap between the rear surface 116c of the raising base 116 and the bottom surface 117a of the housing room 117 as indicated by the arrow $Y_2$, separately from the direction of flow along the mounting surface 116b indicated by the arrow $Y_1$. When a flow amount to the inside of the casing 20 from the opening of the treatment tool channel 115 is the same, it is possible to increase a flow amount of solution that flows on a side of the rear surface 116c indicated by the arrow $Y_2$ by limiting the flow mount (decreasing a flow speed) of solution that flows on a side of the mounting surface 116b indicated by the arrow $Y_1$ by the water wheel 23. Moreover, in a portion on the proximal end side relative to the water wheel 23 out of the first casing 21, a part of an inner surface 213a of the semicylindrical portion 213 protrudes inward in the diameter direction. In the attached state, the protruding inner surface 213a is positioned inside the treatment tool opening 112a that opens to the non-inclined portion 112h of the second hard portion 112. Furthermore, the proximal end portion out of the semicylindrical portion 213 is fastened on its outer periphery by the ring-shaped member 24 together with the proximal end portion of the second casing 22, and the inner periphery portion is in contact with the bending portion 113. This facilitates flow of solution flowing out from the opening of the treatment tool channel 115 to flow in the direction indicated by the arrow $Y_1$.

For example, when the water wheel 23 is not moving during cleaning, a flow of solution indicated by the arrow $Y_1$ does not occur, and the solution flows only in a gap at a portion at which a surface (excluding the mounting surface 116b) of the raising base 116 and a wall surface of the housing room 117 (including the flow indicated by the arrow $Y_2$) face each other. When the water wheel 23 is then rotated by pressure of solution coming from a direction of the treatment tool channel 115, the flow indicated by the arrow $Y_1$ occurs in addition to the flow of solution indicated by the arrow $Y_2$. Moreover, the supporting axis 231 positioned in a rotation center of the water wheel 23 is arranged at a position enabling rotation of the water wheel 23 only in one direction by solution flowing from the opening of the treatment tool channel 115. Therefore, the water wheel 23 rotates only in one direction as a result of occurrence of the flow indicated by the arrow $Y_1$ inside the first casing 21 at cleaning. That is, the water wheel 23 rotates only in a direction in which solution in the housing room 117 flows outside the first casing 21 through the opening window 214. This enables to suppress backflow of solution that has been used to clean the raising base 116 in the housing room 117 to the housing room 117 that has already been cleaned.

Furthermore, as shown in FIG. 6, the raising base 116 is arranged not to be in contact with a side surface 117b of the housing room 117. Therefore, a narrow gap is formed at a portion at which the side surface 117b of the housing room 117 and a side surface 116d of the raising base 116 face each other. When the flow of solution indicated by the arrow $Y_2$ occurs as described above, it is possible to feed solution not only to the narrow gap at the portion at which the rear surface 116c of the raising base 116 and the bottom surface 117a of the housing room 117 face each other, but also into the narrow gap at the portion at which the side surface 116d of the raising base 116 and the side surface 117b of the housing room 117 face each other.

As described, by making cleaning solution flow from the treatment tool channel 115 toward the distal end portion 110, the mounting surface 116b of the raising base 116 can be cleaned, and the solution can be fed also into the narrow gap between a surface (the rear surface 116c and the side surface 116d) of the raising base 116 and a wall surface (the bottom surface 117a and the side surface 117b) of the housing room 117. Thus, it is possible to make solution flow to every corner of a narrow gap formed in the distal end portion 110 that includes the raising base 116, and to clean the surface (the mounting surface 116b, the rear surface 116c, and the side surface 116d) of the raising base 116 housed in the housing room 117 easily with just one feed of water.

As explained above, according to the first embodiment, a flow of solution inside the casing 20 can be restrained (controlled) by the water wheel 23, which is the fluid controller and, therefore, it is possible to promote a flow of solution flowing into a narrow gap between the housing room 117 and the raising base 116. Moreover, because the water wheel 23 is rotatable, solution flows along the mounting surface 116b of the raising base 116 as the water wheel 23 rotates. Thus, by making the cleaning solution flow from the treatment tool inlet 121 of the treatment tool channel 115 of the endoscope 1 toward the treatment tool opening 112a, a flow of solution along the entire surface of the raising base 116 occurs. Therefore, it is possible to distribute solution equally to a narrow gap between the raising base 116 and the housing room 117 and to make the cleaning process of the distal end portion 110 of the endoscope 1 easy.

Figure 8:
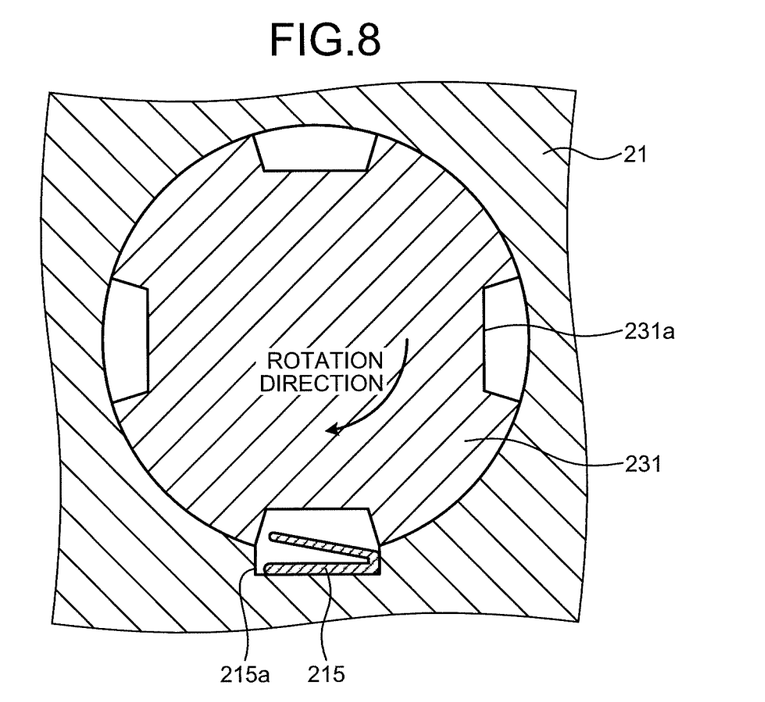
FIG. 8 is a cross-section schematically showing an example of a non-return structure.

It is not limited to a structure that a rotational resistance of the water wheel 23 is generated by the supporting axis 231 sliding on the first casing 21. For example, the attachment 2 in which a rotational resistance of the water wheel 23 is generated by the outer periphery portion 23a of the water wheel 23 sliding on the mounting surface 116b of the raising base 116 can be structured. Alternatively, it can be structured such that a rotational resistance of the water wheel 23 is generated by the outer periphery portion 23a of the water wheel 23 sliding a part of the first casing 21. Furthermore, as for the structure of limiting the rotation direction of the water wheel 23 to one direction, it is not limited to the case in which the supporting axis 231 is positioned at such a position that the water wheel 23 is rotated by a flow of solution only in one direction described above. For example, it can be structured such that a non-return structure, such as a latch, is provided in the supporting axis 231 so that the water wheel 23 rotates only in one direction. FIG. 8 is a cross-section schematically showing an example of a non-return structure. As shown in FIG. 8, a non-return structure in which the supporting axis 231 rotates only in one direction can be structured by arranging a blade spring 215 at an attaching portion of the first casing 21 and the supporting axis 231. In this case, in the first casing 21, a housing concave portion 215a to house the blade spring 215 is formed. At an outer periphery portion of the supporting axis 231, plural engaging concave portions 231a are formed at predetermined intervals along a perimeter direction. The blade spring 215 is arranged inside the housing concave portion 215a, pushed down toward the housing concave portion 215a when the supporting axis 231 rotates in a forward direction (one direction described above). That is, when the supporting axis 231 is about to rotate in a reverse direction, the blade spring 215 protrudes out toward the supporting axis 231 to engage with the engaging concave portion 231a. Thus, the supporting axis 231 becomes rotatable in the forward direction, and the reverse rotation of the supporting axis 231 is restrained.

Moreover, the outer periphery portion 23a of the water wheel 23 is not necessarily required to be in contact with the mounting surface 116b of the raising base 116. The attachment 2 is only required to be structured such that a gap between the outer periphery portion 23a of the water wheel 23 and the mounting surface 116b of the raising base 116 is narrow in the attached state. That is, it is only necessary to arrange the blade wheel 233 so that the gap is narrow, and a flow of solution indicated by the arrow $Y_1$ in FIG. 7 described above can be controlled. Therefore, the attachment 2 can also be structured such that the water wheel 23 and the raising base 116 are not in contact with each other in the attached state.

Furthermore, the shape of the opening window 214 is not limited to the partially curved shape described above, and can be changed to a rectangular shape, a circular shape, or the like as appropriate. Moreover, the water wheel 23 can be structured with a rotating body, such as a gear, not having two pieces of rotating plates 232 as side plates.

2. Modification of First Embodiment

Figure 9:
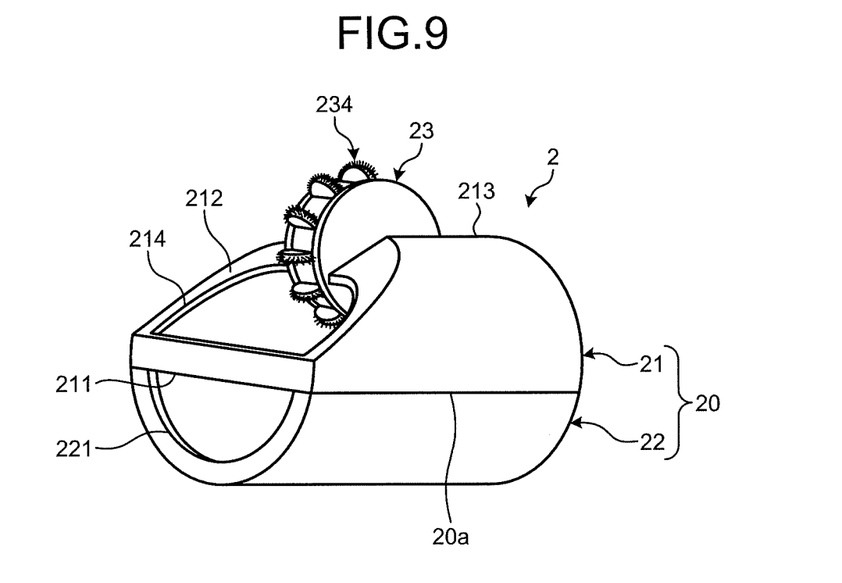
FIG. 9 is a perspective view schematically showing an entire structure of an endoscope tip attachment according to a modification of the first embodiment.

FIG. 9 is a perspective view schematically showing an entire structure of the attachment 2 according to a modification of the first embodiment. As shown in FIG. 9, a cleaning brush 234 is provided in the water wheel 23 in the modification of the first embodiment described above. The brush 234 is made from a material having flexibility, such as an elastic member. Moreover, the brush 234 is made into one piece with the water wheel 23, and protrudes outward in a diameter direction from an outer periphery portion of the blade wheel 233. When this water wheel 23 rotates, the brush 234 slides on the mounting surface 116b of the raising base 116. The brush 234 can be arranged in a whole area of the outer periphery portion 23a, or can be arranged in part of the outer periphery portion 23a. Furthermore, the brush 234 can be arranged to be integrated in a portion between blades of the blade wheel 233 in a perimeter direction to protrude further outward in the diameter direction than the blades.

According to the attachment 2 of the modification, the brush 234 can rub to clean the mounting surface 116b of the raising base 116 as the water wheel 23 rotates. This produces a cleaning effect by the water wheel 23 with a brush in addition to the cleaning effect by a flow of solution.

3. Second Embodiment

Figure 10:
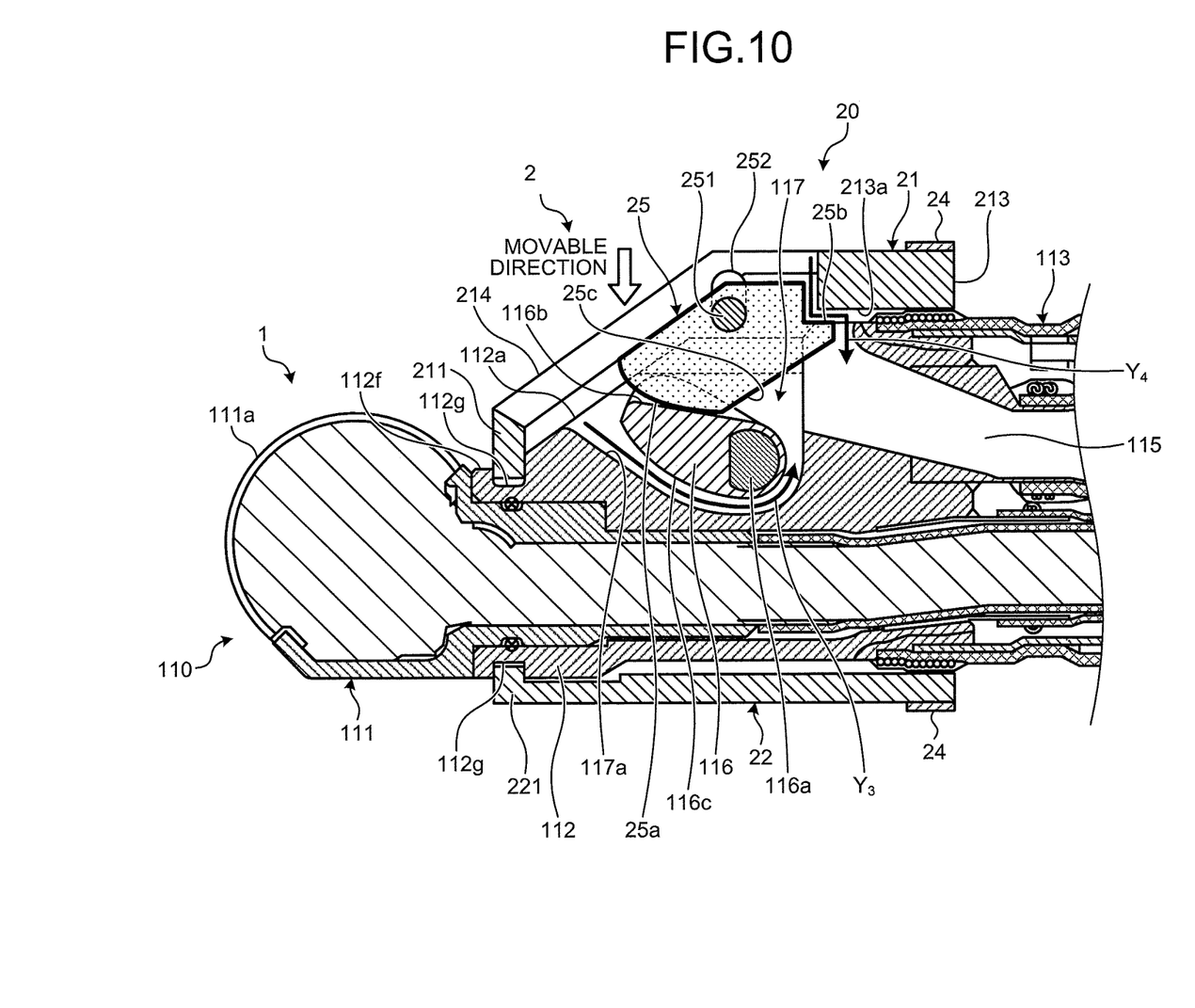
FIG. 10 is a diagram for explaining an endoscope tip attachment according to a second embodiment.
Figure 11:
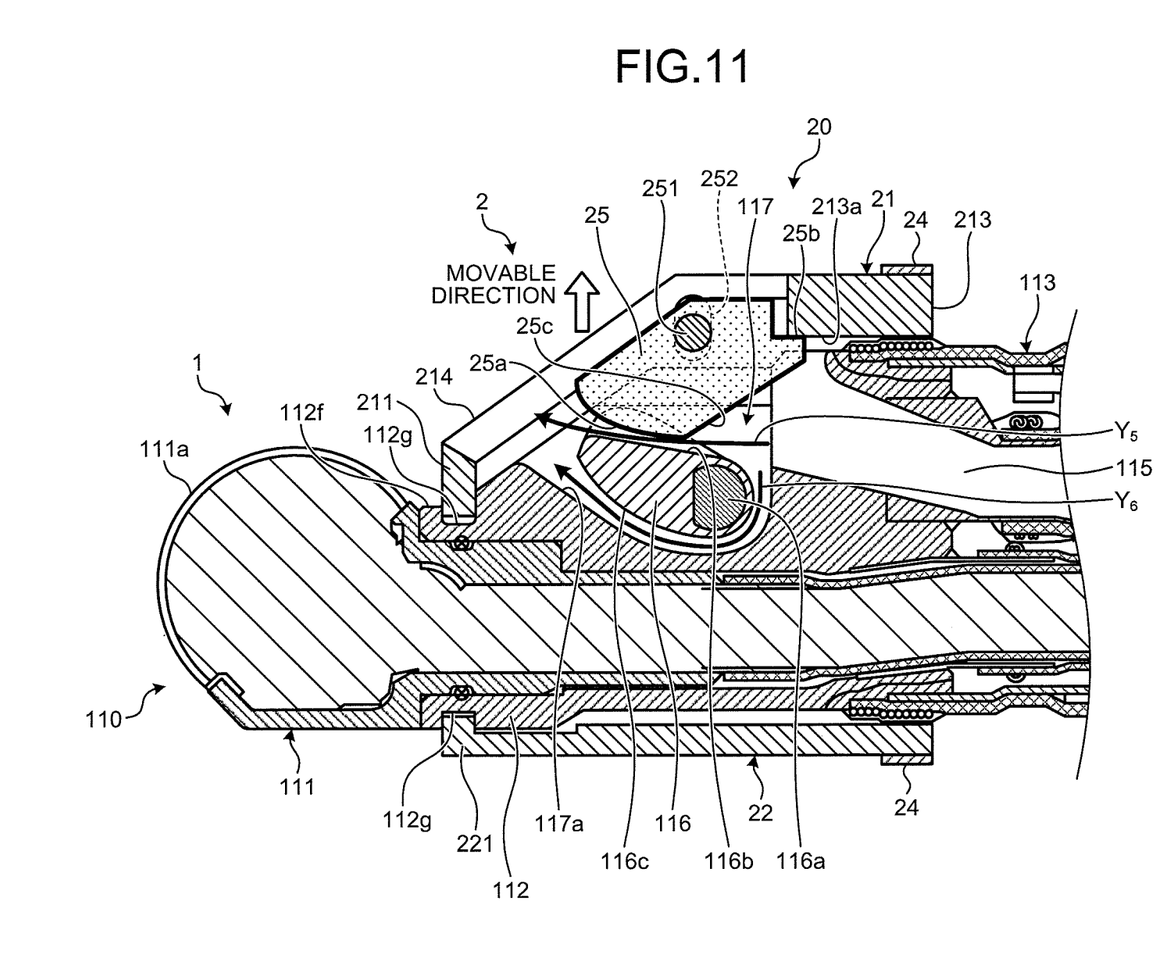
FIG. 11 is a diagram for explaining a flow of solution when an endoscope is cleaned by using the endoscope tip attachment according to the second embodiment.

The attachment 2 according to a second embodiment is explained, referring to FIG. 10 and FIG. 11. FIG. 10 is a diagram for explaining the attachment 2 according to the second embodiment. FIG. 11 is a diagram for explaining a flow of solution when the endoscope 1 is cleaned by using the attachment 2 according to the second embodiment. In explanation of the second embodiment, explanation about components similar to those of the first embodiment is omitted, and the reference symbols thereof are used.

AS shown in FIG. 10, the attachment 2 of the second embodiment includes a valve member 25 that is movable by pressure of solution, in place of the water wheel 23 in the first embodiment. The valve member 25 is a fluid controller, and is attached to the first casing 21 through a supporting member 251 in a state of being housed inside the first casing 21. The supporting member 251 is attached to a guide groove 252 provided in the first casing 21. The valve member 25 and the supporting member 251 are moving objects that integrally move, and are movable in an up-and-down direction (movable direction indicated by an arrow) in FIG. 10 and FIG. 11 along the guide groove 252 linearly formed. For example, the supporting member 251 is constituted of an axial member that penetrate through the valve member 25, and fits in the guide groove 252 at both ends of the axial member. Moreover, the valve member 25 is housed inside the first casing 21. The raising base 116 functions as a first valve mount of the valve member 25, and the semicylindrical portion 213 of the first casing 21 functions as a second valve mount of the valve member 25.

In detail, the valve member 25 has a bottom surface 25a that comes in contact with the mounting surface 116b of the raising base 116, a top surface 25b that comes in contact with the inner surface 213a of the semicylindrical portion 213, and a pressure receiving surface 25c that faces the opening of the treatment tool channel 115. Moreover, the valve member 25 includes an inclined surface that inclines along the inclined portion 212 of the first casing 21.

The bottom surface 25a is curved in a convex shape toward the raising base 116 from the distal end side to the proximal end side of the valve member 25. Furthermore, the bottom surface 25a is curved along the shape of the mounting surface 116b of the raising base 116 (shown in FIG. 6) in a width direction (the axial direction of the supporting axis 116a) of the raising base 116. In a state in which the bottom surface 25a is in contact with the mounting surface 116b as shown in FIG. 10, the valve member 25 is in a first state (a settled state at sucking) of being in contact with the raising base 116, not in Contact with the inner surface 213a of the semicylindrical portion 213 in the first casing 21. In this first state, a flow of solution along the mounting surface 116b of the raising base 116 is interrupted. On the other hand, the valve member 25 and the raising base 116 are not in contact with each other (in a case of a second state described later), the flow is not interrupted.

The top surface 25b is included in a portion protruding toward the proximal end side in the valve member 25, and has a shape along the inner surface 213a of the semicylindrical portion 213. Furthermore, in a diameter direction of the casing 20, the top surface 25b and the inner surface 213a face each other. In a state in which the top surface 25b and the inner surface 213a are in contact with each other as shown in FIG. 11, the valve member 25 is in the second state of being not in contact with the raising base 116, but in contact with the semicylindrical portion 213 (a settled state at water feeding). In this second state, a flow of solution along the top surface 25b from the outside of the semicylindrical portion 213 toward the inside of the first casing 21 is interrupted. On the other hand, when the valve member 25 and the semicylindrical portion 213 are not in contact with each other (in the first state described above), the flow is not interrupted. As described, the attachment 2 in the second embodiment is structured to be able to switch between the first state and the second state.

Moreover, the pressure receiving surface 25c is a surface that receives pressure of solution that has flowed out from the opening of the treatment tool channel 115, and is inclined toward the distal end side from the proximal end side. The valve member 25 is structured such that a direction in which the distal end portion 110 of the endoscope 1 extends (the direction toward the distal ends side from the proximal end side) and the movable direction of the valve member 25 intersect each other because the valve member 25 moves by pressure of solution received on the pressure receiving surface 25c. Therefore, the pressure receiving surface 25c extends to a lower part of a portion at which the valve member 25 and the supporting member 251 are connected, and the inclined direction of the pressure receiving surface 25c is set to a direction intersecting the movable direction of the valve member 25.

A flow of solution at cleaning is explained herein, referring to FIG. 10 and FIG. 11.

The state shown in FIG. 10 is a case of cleaning the distal end portion 110 of the endoscope 1 in cleaning solution, and is a state in which solution outside the casing 20 is sucked from the opening of the treatment tool channel 115 by sucking solution inside the treatment tool channel 115 from the treatment tool inlet 121 (shown in FIG. 1). When solution inside the casing 20 is sucked from the opening of the treatment tool channel 115, pressure of solution by suction acts on the pressure receiving surface 25c to move the valve member 25 to approach to the raising base 116. The valve member 25 then comes in contact with (settled on)

the raising base 116. By thus closing the gap between the mounting surface 116b of the raising base 116 and the bottom surface 25a of the valve member 25 with the valve member 25 at the distal end side the raising base 116, the flow of solution is restrained. In this case, solution that has flowed inside the casing 20 through the opening window 214 from the outside of the casing 20 is to flow through a gap between the surface of the raising base 116 (the rear surface 116c and the side surface 116d) and the wall surface (the bottom surface 117a and the side surface 117b) of the housing room 117. That is, a flow of solution indicated by an arrow $Y_3$ in FIG. 10 occurs, and the solution flows from the distal end side to the proximal end side along the rear surface 116c of the raising base 116. As a result, solution outside the casing 20 is sucked into the treatment tool channel 115 through a portion on a side of the rear surface 116c of the raising base 116. The arrow $Y_3$ shown in FIG. 10 indicates a direction in which solution flows in the gap at the portion at which the surface (excluding the mounting surface 116b) of the raising base 116 and the wall surface of the housing room 117 face each other. On the other hand, as the bottom surface 25a of the valve member 25 and the mounting surface 116b of the raising base 116 come in contact with each other, a gap is generated between the top surface 25b of the valve member 25 and the inner surface 213a of the proximal end portion (the semicylindrical portion 213) of the first casing 21. Therefore, solution outside the casing 20 flows into the inside of the casing 20 also through another path different from the path of flowing from the distal end side of the raising base 116 described above. As indicated by an arrow $Y_4$ in FIG. 10, solution outside the casing 20 flows into the treatment tool channel 115 through a gap between the top surface 25b and the inner surface 213a. The arrow $Y_4$ shown in FIG. 10 indicates a direction in which solution flows through a gap at the portion at which the top surface 25b and the inner surface 213a of the semicylindrical portion 213 face each other at the distal end side of the valve member 25.

The state shown in FIG. 11 is a case in which the distal end portion 110 of the endoscope 1 is cleaned in atmosphere, and is a state in which solution flows in a reverse direction to the flowing direction of the solution shown in FIG. 10 (a water feeding state). The water feeding state is when solution is fed from the treatment tool inlet 121 to flow toward the opening of the treatment tool channel 115 at cleaning. In this case, the valve member 25 moves in a direction opposite to the raising base 116 because it receives pressure of solution flowing out from the opening of the treatment tool channel 115 on the pressure receiving surface 25c. Thus, a gap is generated between the bottom surface 25a of the valve member 25 and the mounting surface 116b of the raising base 116. As a result, solution flows toward the opening window 214 from the treatment tool channel 115 through the gap as indicated by the arrow $Y_5$ in FIG. 11. The arrow $Y_5$ shown in FIG. 11 indicates a direction in which solution flows through the gap at a portion at which the valve member 25 and the mounting surface 116b of the raising base 116 face each other. On the other hand, the gap at a portion at which the valve member 25 and the semicylindrical portion 213 face each other is closed as the inner surface 213a on the proximal end side of the first casing 21 and the top surface 25b of the valve member 25 come into contact with each other. Therefore, solution that has flowed into the inside of the casing 20 flows through a gap between the rear surface of the raising base 116 and the bottom surface 117a of the housing room 117 toward the distal end side from the proximal end side as indicated by the arrow $Y_6$. The arrow $Y_6$ in FIG. 11 indicates a direction in which solution flows toward the distal end side from the proximal end side through the gap at the portion at which the surface (excluding the mounting surface 116b) of the raising base 116 and the wall surface of the housing room 117 face each other.

As explained above, according to the second embodiment, a flow of solution inside the casing 20 can be controlled by the valve member 25, which is the fluid controller and, therefore, it is possible to promote a flow of solution flowing into a gap between the housing room 117 and the raising base 116. Moreover, because the valve member 25 is movable, solution flows along the mounting surface 116b of the raising base 116 as the valve member 25 moves away from the raising base 116. Thus, the cleaning solution flows from the treatment tool channel 115 of the endoscope 1 toward the treatment tool opening 112a, and a flow of solution along the entire surface of the raising base 116 from the proximal end side to the distal end side occurs. Alternatively, by sucking solution from the treatment tool channel 115 in a state in which the distal end portion 110 is immersed in cleaning solution, a flow of solution that flows into a narrow gap between the housing room 117 and the raising base 116 from the distal end side toward the proximal end side occurs. As a result, a flow of solution along the entire surface of the raising base 116 occurs. As described, it is possible to distribute solution equally to a narrow gap between the raising base 116 and the housing room 117, and to make the cleaning process of the distal end portion 110 of the endoscope 1 easy.

In the embodiments described above, a case in which the attachment 2 is attached to the distal end portion 110 in the cleaning process has been explained, but the attachment 2 can be used in a sterilization process of the endoscope also. In this case, "cleaning solution" in the explanation above can be read as "sterilization solution".

Moreover, an endoscope to which the attachment 2 can be attached is not limited to the ultrasound endoscope described above. That is, as long as it is an endoscope having a raising base at a distal end portion, it can be a side-viewing endoscope or an oblique-viewing endoscope. Furthermore, various types of endoscopes to observe digestive canals (the esophagus, the duodenum, the large intestine), respiratory organs (the trachea, the bronchus), and the like of a subject are included.

According to the disclosure, at cleaning of a distal end portion of an endoscope, a flow of solution can be controlled inside a casing by a fluid controller and, therefore, a flow of solution flowing along an entire surface of a raising base can be promoted. Moreover, because the fluid controller is movable, by making cleaning solution flow from a treatment-tool insertion channel of the endoscope toward an opening thereof, a flow of solution along the entire surface of the raising base inside the casing occurs. Thus, it is possible to feed the cleaning solution to every corner equally at the distal end portion of the endoscope having the raising base, to make a cleaning process easy.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope tip attachment comprising:
 a cylindrical casing arranged to surround a distal end portion of an endoscope, the endoscope including a raising base configured to raise a treatment tool; and
 a fluid controller having one or more pressure receiving surfaces, the fluid controller being positioned at an opening of a treatment-tool insertion channel of the endoscope in a state in which the casing is attached to the distal end portion of the endoscope, the fluid controller being configured to control a flow of solution that has flowed from the treatment-tool insertion channel of the endoscope toward the distal end portion of the endoscope to flow along a surface of the raising base provided at the distal end portion of the endoscope, the one or more pressure receiving surfaces being movable by pressure received from the solution;
 wherein the fluid controller comprises a water wheel attached to the casing through a supporting axis, the water wheel being configured to be rotated by pressure received from the solution flowing out from the opening of the treatment-tool insertion channel toward the distal end portion of the endoscope.

2. The endoscope tip attachment according to claim 1, further comprising a latch enabling the water wheel to rotate only in one direction at an attachment portion of the supporting axis and the casing.

3. The endoscope tip attachment according to claim 1, wherein the supporting axis is arranged at a position at which the water wheel is rotated only in one direction by pressure received from the solution flowing out from the opening of the treatment-tool insertion channel toward the distal end portion of the endoscope.

4. The endoscope tip attachment according to claim 1, wherein the supporting axis is configured to slide on the casing when the water wheel rotates.

5. The endoscope tip attachment according to claim 1, wherein an outer periphery portion of the water wheel is configured to come in contact with a surface of the raising base.

6. The endoscope tip attachment according to claim 1, wherein the water wheel has a brush provided in an integrated manner.

7. The endoscope tip attachment according to claim 1, wherein the casing includes
 a fitting portion configured to fit in a groove provided at the distal end portion of the endoscope; and
 an opening window provided between a portion at which the fluid controller is attached and the fitting portion.

8. The endoscope tip attachment according to claim 1, wherein the casing includes
 a first casing to which the fluid controller is attached; and
 a second casing detachable with respect to the first casing.

9. An endoscope system comprising:
 an endoscope having a distal end portion; and
 a tip attachment comprising:
  a cylindrical casing disposed at a distal end portion of an endoscope, the endoscope including a raising base configured to raise a treatment tool; and
  one or more pressure receiving surfaces disposed within the casing and configured to receive a flow of solution from an opening of a treatment-tool insertion channel of the endoscope in a first state in which the casing is attached to the distal end portion of the endoscope;
 wherein the raising base having a first surface over which the solution flows in a second state in which the casing is not attached to the distal end portion of the endoscope;
 in the first state, the one or more pressure receiving surfaces being configured to move by pressure received from the flow of solution to divert at least a portion of the flow of solution to a second surface of the raising base, the second surface being different from the first surface; and
 the one or more pressure receiving surface comprises one or more paddles of a water wheel rotatably arranged on the casing.

10. The endoscope system according to claim 9, wherein:
 the first surface comprises a lifting surface of the raising base configured to raise the treatment tool; and
 the second surface comprises an adjacent surface of the lifting base positioned adjacent to a wall of the distal end portion of the endoscope.

* * * * *